US012766241B2

(12) United States Patent
Marass

(10) Patent No.: US 12,766,241 B2
(45) Date of Patent: Oct. 20, 2026

(54) IRRIGATED CATHETER SYSTEM INCLUDING FLUID DEGASSING APPARATUS AND METHODS OF USING SAME

(71) Applicant: ST. JUDE MEDICAL, CARDIOLOGY DIVISION, INC., St. Paul, MN (US)

(72) Inventor: Timothy S. Marass, Minneapolis, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 1240 days.

(21) Appl. No.: 17/623,774

(22) PCT Filed: Sep. 25, 2020

(86) PCT No.: PCT/US2020/052609
§ 371 (c)(1),
(2) Date: Dec. 29, 2021

(87) PCT Pub. No.: WO2021/062074
PCT Pub. Date: Apr. 1, 2021

(65) Prior Publication Data

US 2022/0241490 A1 Aug. 4, 2022

Related U.S. Application Data

(60) Provisional application No. 62/907,017, filed on Sep. 27, 2019.

(51) Int. Cl.
*A61B 18/14* (2006.01)
*A61B 18/00* (2006.01)
(Continued)

(52) U.S. Cl.
CPC ....... *A61M 3/0208* (2014.02); *A61B 18/1492* (2013.01); *A61M 3/022* (2014.02);
(Continued)

(58) Field of Classification Search
CPC .. A61M 3/0208; A61M 3/022; A61M 3/0258; A61M 2205/7536; A61M 5/36;
(Continued)

(56) References Cited

U.S. PATENT DOCUMENTS 4,908,048 A 3/1990 Hofmann et al.
6,508,859 B1 * 1/2003 Zia ........................ A61M 5/385 96/219

(Continued)

FOREIGN PATENT DOCUMENTS

EP 0187683 A2 7/1986
WO 2014022149 A1 2/2014

OTHER PUBLICATIONS

International Search Report and Written Opinion, PCT/US2020/052609, Dec. 1, 2021, 16 pages.

*Primary Examiner* — Joseph A Stoklosa
*Assistant Examiner* — Adam J Avigan
(74) *Attorney, Agent, or Firm* — Dentons Durham Jones Pinegar

(57) ABSTRACT

Disclosed herein is an irrigated catheter system. The system includes a catheter shaft including a fluid delivery tube, an electrode coupled to the catheter shaft at a distal end thereof and in fluid communication with the fluid delivery tube, a fluid source coupled in fluid communication with the fluid delivery tube for supplying fluid thereto, and a fluid degassing apparatus fluidly coupled between the fluid source and the fluid delivery tube such that the fluid flows through the fluid degassing apparatus. The fluid degassing apparatus includes one of a gas filter including a permeable membrane
(Continued)

disposed in a fluid-tight housing, a centrifugal separator, and a multi-chamber system including a vacuum chamber and a fluid reservoir fluidly coupled downstream of the vacuum chamber.

13 Claims, 5 Drawing Sheets

(51) Int. Cl.
*A61M 3/02* (2006.01)
*B01D 19/00* (2006.01)

(52) U.S. Cl.
CPC ....... *A61M 3/0258* (2013.01); *B01D 19/0031* (2013.01); *B01D 19/0036* (2013.01); *B01D 19/0052* (2013.01); *B01D 19/0063* (2013.01); *A61B 2018/00577* (2013.01); *A61B 2218/002* (2013.01); *A61M 2205/7536* (2013.01)

(58) Field of Classification Search
CPC ................. A61M 5/38; A61B 18/1492; A61B 2018/00577; A61B 2218/002; A61B 2018/00351; A61B 2217/007; A61B 18/1206; B01D 19/0031; B01D 19/0036; B01D 19/0052; B01D 19/0063; A61F 7/12; A61F 2007/126
See application file for complete search history.

(56) References Cited

U.S. PATENT DOCUMENTS

| | | | | |
|---|---|---|---|---|
| 7,263,397 | B2 * | 8/2007 | Hauck | A61B 5/065 600/509 |
| 9,173,987 | B2 | 11/2015 | Meyer et al. | |
| 10,307,201 | B2 | 6/2019 | Curley | |
| 2009/0163864 | A1 * | 6/2009 | Breznock | A61M 5/36 604/122 |
| 2010/0331779 | A1 * | 12/2010 | Nystrom | A61M 5/14546 604/125 |
| 2015/0351823 | A1 * | 12/2015 | Curley | A61B 18/16 606/28 |

* cited by examiner

IRRIGATED CATHETER SYSTEM INCLUDING FLUID DEGASSING APPARATUS AND METHODS OF USING SAME

CROSS REFERENCE TO RELATED APPLICATIONS

This application claims priority to international application No. PCT/US2020/052609, filed Sep. 25, 2020, which claims priority to provisional application Ser. No. 62/907,017, filed Sep. 27, 2019, both of which are incorporated herein by reference in their entirety.

BACKGROUND OF THE DISCLOSURE a. Field of the Disclosure

The present disclosure relates generally to irrigated catheter systems and methods of using irrigated catheter systems. More particularly, the present disclosure relates to fluid degassing apparatus for removing gas from fluid supplied to irrigated catheter systems during medical procedures, such as ablation and/or mapping procedures.

b. Background

Tissue ablation may be used to treat a variety of clinical disorders. For example, tissue ablation may be used to treat cardiac arrhythmias by destroying aberrant pathways that would otherwise conduct abnormal electrical signals to the heart muscle. Several ablation techniques have been developed, including cryoablation, microwave ablation, radio frequency (RF) ablation, and high frequency ultrasound ablation. RF ablation has become increasingly popular for many symptomatic arrhythmias such as AV nodal reentrant tachycardia, AV reciprocating tachycardia, idiopathic ventricular tachycardia, and primary atrial tachycardias. RF ablation is also a common technique for treating disorders of the endometrium and other body tissues including the brain.

A typical RF ablation system includes an RF ablation generator, which feeds current to a catheter containing a conductive tip electrode for contacting targeted tissue. In some systems, an irrigation fluid or irrigant can be supplied to the conductive tip electrode and/or around the target tissue, for example, to provide cooling to the electrode and prevent overheating. While such irrigant can generally provide suitable thermal management at the target tissue site, gas present or dissolved within the fluid can reduce the effectiveness of the catheter system. For example, gas dissolved in irrigant fluid can come out of solution as the fluid flows through the catheter system (e.g., due to rapid pressure changes, heating, etc.), and accumulate at the catheter tip. If these gas bubbles form around a temperature sensor of the catheter system, the gas can insulate the sensor and lead to inaccurate (e.g., higher) temperature readouts. Accordingly, a need exists for improved irrigated catheter systems and methods.

SUMMARY OF THE DISCLOSURE

The present disclosure is directed to an irrigated catheter system including a catheter shaft including a fluid delivery tube, an electrode coupled to the catheter shaft at a distal end thereof and in fluid communication with the fluid delivery tube, a fluid source coupled in fluid communication with the fluid delivery tube for supplying fluid thereto, and a fluid degassing apparatus fluidly coupled between the fluid source and the fluid delivery tube such that the fluid flows through the fluid degassing apparatus. The fluid degassing apparatus includes one of a gas filter including a permeable membrane disposed in a fluid-tight housing, a centrifugal separator, and a multi-chamber system including a vacuum chamber and a fluid reservoir fluidly coupled downstream of the vacuum chamber.

The present disclosure is further directed to a method of supplying fluid to an irrigated catheter system. The method includes coupling a fluid source in fluid communication with a fluid delivery tube of a catheter shaft, where the catheter shaft includes an electrode coupled to a distal end thereof and in fluid communication with the fluid delivery tube. The method further includes fluidly coupling a fluid degassing apparatus between the fluid source and the fluid delivery tube. The fluid degassing apparatus includes one of a gas filter including a permeable membrane disposed in a fluid-tight housing, a centrifugal separator, and a multi-chamber system including a vacuum chamber and a fluid reservoir fluidly coupled downstream of the vacuum chamber. The method further includes directing fluid from the fluid source through the fluid degassing apparatus such that gas is removed from the fluid, and supplying the degassed fluid to the fluid delivery tube.

The present disclosure is further directed to an irrigated ablation catheter system including a catheter shaft including a fluid delivery tube, an ablation electrode coupled to the catheter shaft at a distal end thereof and in fluid communication with the fluid delivery tube, an ablation generator electrically coupled to the electrode and configured to supply ablative energy thereto, a fluid source coupled in fluid communication with the fluid delivery tube, a pump coupled in fluid communication with the fluid source and configured to pump fluid from the fluid source to the fluid delivery tube, and a fluid degassing apparatus fluidly coupled between the fluid source and the fluid delivery tube such that the fluid flows through the fluid degassing apparatus. The fluid degassing apparatus includes one of a gas filter including a permeable membrane disposed in a fluid-tight housing, a centrifugal separator, and a multi-chamber system including a vacuum chamber and a fluid reservoir fluidly coupled downstream of the vacuum chamber.

DETAILED DESCRIPTION OF THE DISCLOSURE

The present disclosure is directed to irrigated catheter systems and methods and, more particularly, to fluid degassing apparatus for removing gas from fluid supplied to irrigated catheter systems during medical procedures, such as ablation and/or mapping procedures. Embodiments of the systems and methods disclosed herein facilitate improving catheter procedures by improving the accuracy of catheter sensor data and reducing the likelihood of formation of air embolisms. In particular, the catheter systems and methods disclosed herein utilize in-line fluid degassing apparatus to remove, reduce, and/or eliminate gas from fluid supplied to the catheter during medical procedures, such as irrigant fluid. By removing or reducing gas from the fluid, the systems and methods herein reduce the likelihood of gas bubbles accumulating within the catheter system, which could otherwise cause inaccurate temperature sensor readouts and/or formation of gas bubbles that can lead to air embolisms.

Figure 1:
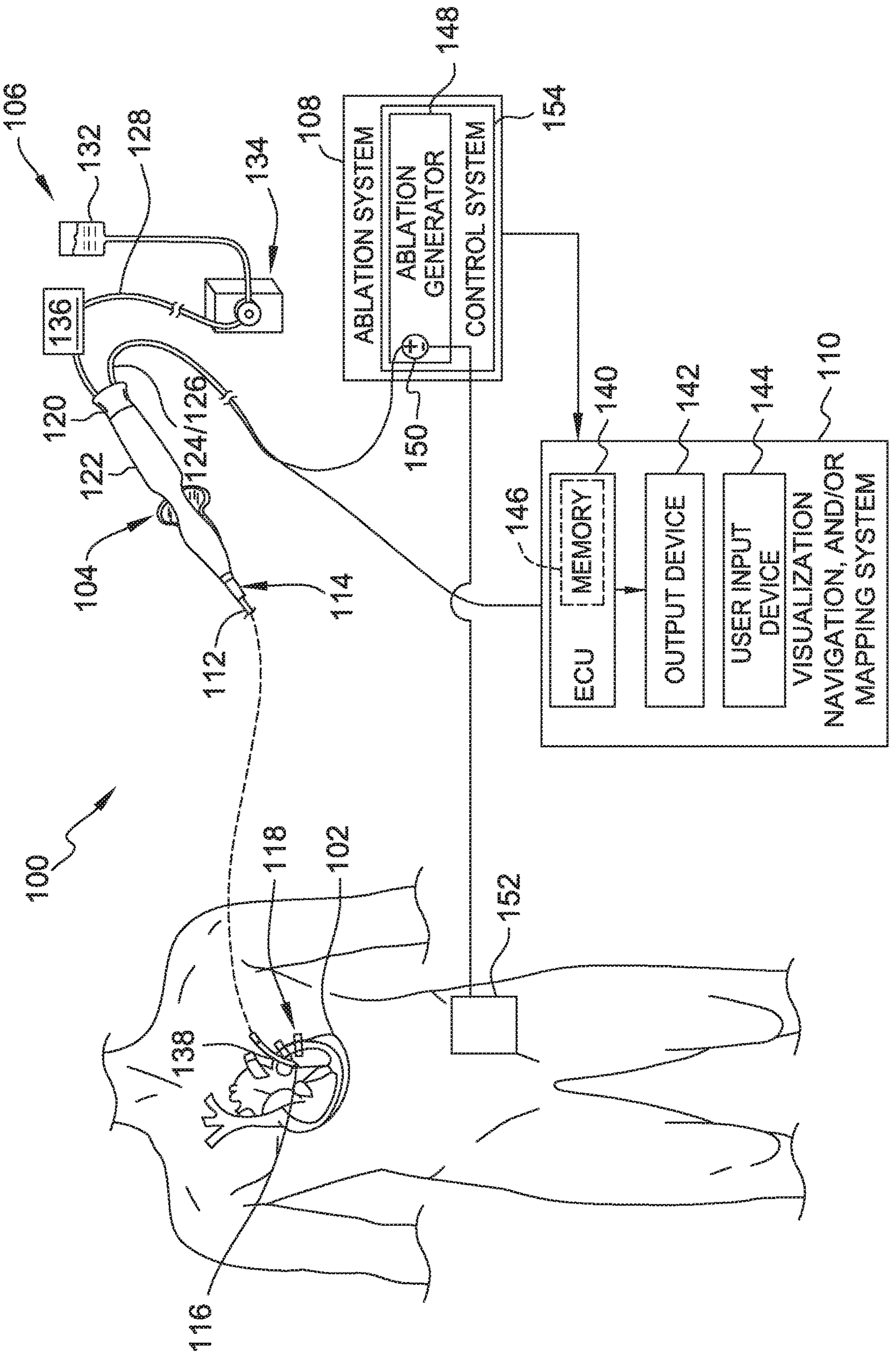
FIG. 1 is a schematic and block diagram view of an irrigated catheter system.

Referring now to the drawings, FIG. 1 illustrates one exemplary embodiment of an irrigated catheter system 100 for examination, diagnosis, and/or treatment of internal body tissues (e.g., targeted tissue 102). In the illustrated embodiment, the tissue 102 is heart or cardiac tissue. It should be understood, however, that the system 100 has equal applicability to procedures (e.g., ablation and/or mapping procedures) on other tissues as well, and is not limited to procedures on cardiac tissue. The system 100 includes a medical device (such as, for example, a catheter 104), a fluid supply system 106 for supplying fluid (e.g., irrigation fluid) to the medical device, an ablation system 108, and a visualization, navigation, and/or mapping system 110.

The catheter 104 is provided for examination, diagnosis, and/or treatment of internal body tissues, such as cardiac tissue 102. In an exemplary embodiment, the catheter 104 comprises a radio frequency (RF) ablation catheter. It should be understood, however, that the catheter 104 is not limited to an RF ablation catheter. Rather, in other embodiments, the catheter 104 may comprise other types of ablation catheters (e.g., cryoablation, ultrasound, irreversible electroporation, balloon, basket, single electrode, bullet, etc.) and/or other types of catheters, such as visualization and/or mapping catheters.

The catheter 104 includes a catheter shaft 112 having a proximal end 114 and a distal end 116 (as used herein, “proximal” refers to a direction toward the end of the catheter 104 near an operator, and “distal” refers to a direction away from the operator and (generally) inside the body of a subject or patient). The shaft 112 is generally an elongated, tubular, flexible member configured for movement within the patient. The shaft 112 supports, for example and without limitation, an electrode 118, associated conductors, and possibly additional electronics used for signal processing or conditioning. The shaft 112 may also permit transport, delivery and/or removal of fluids (including irrigation fluids, cryogenic ablation fluids, and bodily fluids), medicines, and/or surgical tools or instruments. The shaft 112 may be made from conventional materials such as polyurethane, and defines one or more lumens configured to house and/or transport at least electrical conductors, fluids, or surgical tools. The shaft 112 may be introduced into cardiac tissue 102 through a conventional introducer. The shaft 112 may then be steered or guided within cardiac tissue 102 to a desired location with guidewires or other means known in the art.

The catheter 104 may also include a cable connector or interface 120, a handle 122, and one or more electrodes or electrode assemblies 118 mounted in or on the shaft 112 of the catheter 104. In an exemplary embodiment, the electrode 118 is disposed at or near the distal end 116 of the shaft 112, with the electrode 118 comprising an ablation electrode disposed at the extreme distal end 116 of the shaft 112 for contact with cardiac tissue 102. The catheter 104 may further include other conventional components such as, for example and without limitation, sensors, additional electrodes (e.g., ring electrodes) and corresponding conductors or leads, thermocouples, or additional ablation elements, e.g., a high intensity focused ultrasound ablation element and the like.

The connector 120 provides mechanical, fluid, and electrical connection(s) for cables 124, 126, 128 extending from the fluid supply system 106, the ablation system 108, and/or other systems and/or sub-systems of the catheter system 100. The connector 120 is disposed at the proximal end of the catheter 104.

The handle 122 provides a location for the operator to hold catheter 104 and may further provide means for steering or guiding the shaft 112 within the patient. For example, the handle 122 may include means to change the length of a guidewire extending through catheter 104 to distal end 116 of shaft 112 to steer shaft 112. In another exemplary embodiment, the catheter 104 may be robotically driven or controlled. Accordingly, rather than an operator manipulating a handle to steer or guide the catheter 104, and the shaft 112 thereof, in particular, a robot is used to manipulate the catheter 104.

Figure 2:
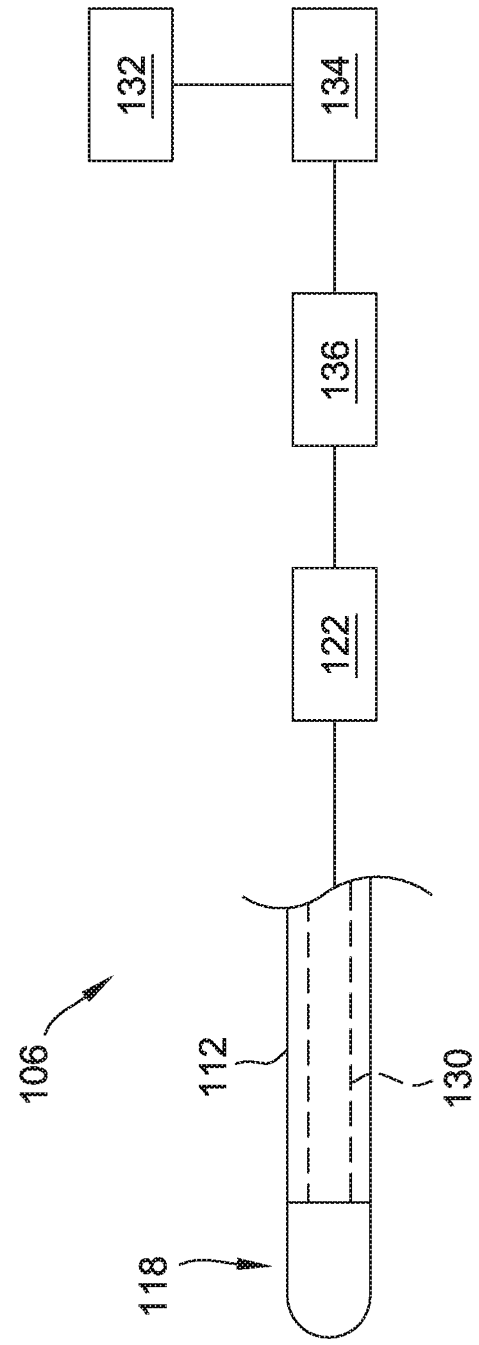
FIG. 2 is a schematic view of a fluid supply system of the irrigated catheter system of FIG. 1.

The catheter 104 further includes at least one fluid lumen or fluid delivery tube 130 (FIG. 2) disposed within the catheter shaft 112. The fluid delivery tube 130 is configured to supply fluid to the distal end of the catheter shaft and/or to the one or more electrodes 118. The fluid delivery tube 130 is connected to the fluid supply system 106, which supplies a suitable fluid (e.g., irrigation fluid) to the fluid delivery tube 130.

In the exemplary embodiment, the fluid supply system 106 includes a fluid source 132 that provides a biocompatible fluid such as saline, or a medicament, and a pump 134 fluidly connected to the fluid source 132 and configured to pump the fluid from the fluid source 132 to the fluid delivery tube 130. The pump 134 may include, for example and without limitation, a fixed rate roller pump or variable volume syringe pump with a gravity feed supply from the fluid source for irrigation. In accordance with the present disclosure, the fluid supply system 106 further includes a fluid degassing apparatus 136 fluidly coupled between the fluid delivery tube 130 and the fluid source 132. As described further herein, the fluid degassing apparatus 136 is configured to remove and/or eliminate gasses from the fluid source as the fluid is fed to the catheter 104, and thereby prevent formation of gas bubbles within the catheter system 100 during use (e.g., during an ablation procedure).

The catheter 104 can further include one or more positioning electrodes 138 mounted in or on the catheter shaft 112. The electrodes 138 can comprise, for example, ring electrodes. The electrodes 138 can be used, for example, with the visualization, navigation, and/or mapping system 110. The electrodes 138 can be configured to provide a signal indicative of both a position and orientation of at least a portion of the catheter shaft 112. The visualization, navigation, and/or mapping system 110 with which the electrodes 138 can be used can comprise an electric field-based system, or, sometimes referred to as an impedance based system, such as, for example, that having the model name EnSite NAVX™ system and commercially available from Abbott Laboratories, and as generally shown with reference to U.S. Pat. No. 7,263,397 titled “Method and Apparatus for Catheter Navigation and Location and Mapping in the Heart," the entire disclosure of which is incorporated herein by reference. The visualization, navigation, and/or mapping system 110 can also include other commercially available systems, including the EnSite™ Velocity™ or EnSite Precision™ cardiac mapping and visualization systems of Abbott Laboratories. In other exemplary embodiments, the visualization, navigation, and/or mapping system 110 can comprise other types of systems, such as, for example and without limitation: a magnetic field-based system such as the CARTO System (now in a hybrid form with impedance- and magnetically-driven electrodes) available from Biosense Webster, or the gMPS system from MediGuide Ltd. In accordance with a combination electric field-based and magnetic field-based system, the catheter can include both electrodes 138 as impedance-based electrodes and one or more magnetic field sensing coils. Commonly available fluoroscopic, computed tomography (CT), and magnetic resonance imaging (MRI)-based systems can also be used.

The visualization, navigation, and/or mapping system 110 can include an electronic control unit (ECU) or controller 140, an output device 142 (e.g., a display), and a user input device 144. The controller 140 can comprise a programmable microprocessor or microcontroller, but can alternatively comprise an application specific integrated circuit (ASIC). The controller 140 can include a central processing unit (CPU) and an input/output (I/O) interface through which the controller 140 can receive input data and can generate output data. The controller 140 can also have a memory 146, and the input data and/or output data acquired and generated by the controller 140 can be stored in the memory 146 of the controller 140.

The ablation system 108 can include, for example, an ablation generator 148 and one or more ablation patch electrodes 152. The ablation generator 148 generates, delivers, and controls ablation energy (e.g., RF) output by the catheter system 100 and the electrode 118. In an exemplary embodiment, the generator 148 can include an RF ablation signal source 150 configured to generate an ablation signal that is output across a pair of source connectors: a positive polarity connector SOURCE (+), which electrically connects to the electrode 118; and a negative polarity connector SOURCE (−), can be electrically connected to one or more of the patch electrodes 152. It should be understood that the term connectors as used herein does not imply a particular type of physical interface mechanism, but is rather broadly contemplated to represent one or more electrical nodes (including multiplexed and de-multiplexed nodes). The source is configured to generate a signal at a predetermined frequency in accordance with one or more user specified control parameters (e.g., power, time, etc.) and under the control of various feedback sensing and control circuitry. The source can generate a signal, for example, with a frequency of about 450 kHz or greater for RF energy.

The ablation system 108 can further include a control system 154 capable of monitoring various parameters associated with the ablation procedure including, for example, impedance, the temperature at the distal tip of the catheter, applied ablation energy, and the position of the catheter, and providing feedback to the operator or another component within system 100 regarding these parameters. In some embodiments, for example, the control system 154 is configured to determine the temperature of the targeted tissue 102 (i.e., the tissue to be ablated) and/or an appropriate ablation technique. The ablation generator 148 can form part of the control system 154 in accordance with some embodiments, or can be separate from the control system 154 in other embodiments.

Devices for determining pressure, temperature, and a flow parameter of a flowing fluid can be used to monitor and/or control the quantity of flow of irrigation fluid within or from the catheter at one or more locations using a flow-from pressure algorithm as known to those of ordinary skill in the art. These devices for determining pressure, temperature, and a flow parameter of a flowing fluid can also be connected to the control system 154.

The energy provided to the ablation electrode 118 can be increased by the control system 154 by increasing the power and/or length of energy delivery (e.g., amplitude and/or operating time) during the ablation cycle. The energy provided to the ablation electrode 118 can be decreased by decreasing the power and/or length of time of energy delivery (e.g., frequency and/or operating time) during the ablation cycle. The ablation technique that is selected by the control system 154 can be selected to produce a certain, predetermined temperature in the targeted tissue 102 that will form a desired lesion in the targeted tissue 102. While the desired lesion can be transmural in some embodiments, the characteristics of the desired lesion can vary significantly. The certain, predetermined temperature in the targeted tissue 102 that will form a desired lesion in the targeted tissue 102 can be affected by the thermal response of the targeted tissue. The thermal response of the targeted tissue 102 can be affected by a number of variables including tissue thickness, amount of fat and muscle, blood flow through the region, and blood flow at the interface of the ablation electrode 118 and the targeted tissue 102.

The control system 154 may include, for example and without limitation, a controller or electronic control unit (ECU), an output device, a user input device, and memory. These components may be the same as or different from the components of the visualization, navigation, and/or mapping system 110. In some embodiments, for example, the control system 154 may be implemented in combination with, as part of, or incorporated within other systems and/or sub-systems of the catheter system 100 including, for example and without limitation, imaging systems, mapping systems, navigation systems (e.g., the visualization, navigation, and/or mapping system 110), and any other system or sub-system of the catheter system 100. Alternatively, as shown in FIG. 1, the control system 154 may be implemented separately from the imaging, mapping, and navigation systems of the catheter system 100.

The catheter system 100 can include other conventional components such as, for example and without limitation, conductors associated with the electrodes, and possibly additional electronics used for signal processing, visualization, localization, and/or conditioning. The catheter system 100 can further include multiple lumens for receiving additional components.

Figure 3:
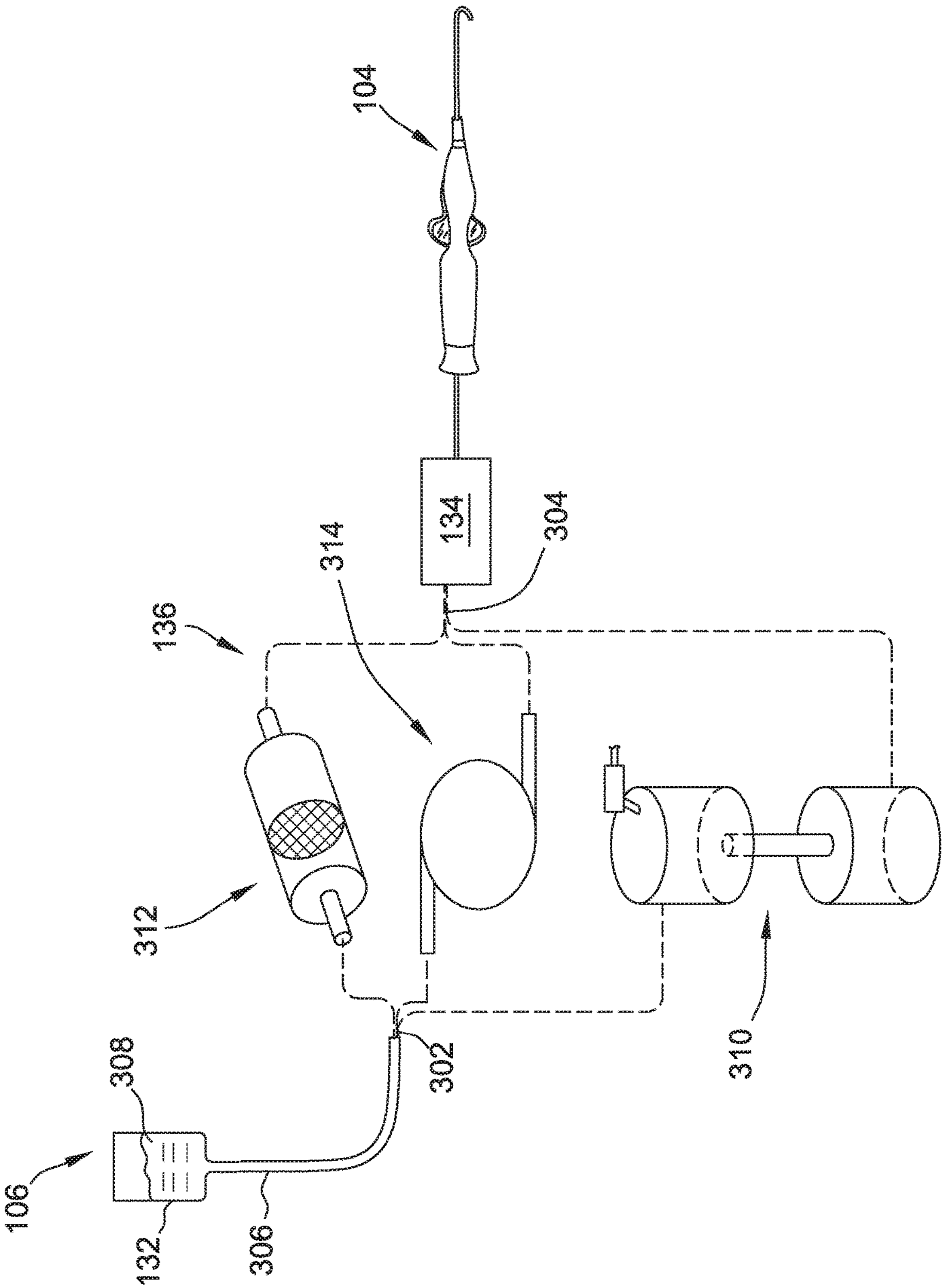
FIG. 3 is another schematic view of the fluid supply system of FIG. 2 illustrating exemplary fluid degassing apparatus suitable for use with the irrigated catheter system of FIG. 1.

With additional reference to FIG. 3, the fluid degassing apparatus 136 is fluidly coupled between the fluid source 132 and the catheter 104. The fluid degassing apparatus 136 includes a fluid inlet 302 and a fluid outlet 304 for fluidly coupling the fluid degassing apparatus 136 in line with the fluid source 132 and the fluid delivery tube 130. The fluid degassing apparatus 136 receives fluid from the fluid source 132 via the fluid inlet 302, and supplies fluid to the catheter 104 (e.g., through the pump 134 or suitable fluid conduits) via the fluid outlet 304. In the illustrated embodiment, the fluid inlet 302 is coupled to a fluid supply line 306 extending from the fluid source 132, and the fluid outlet 304 is coupled to the pump 134. In other embodiments, the fluid inlet 302 and the fluid outlet 304 may be coupled to any other suitable portion of the fluid supply system 106 that enables the catheter system 100 to function as described herein. In some embodiments, the fluid inlet 302 and/or the fluid outlet 304 includes suitable leak-free fluid fittings, such as Luer fittings or adapters, to facilitate connecting and disconnecting the fluid degassing apparatus 136 to and from the catheter system 100.

The fluid degassing apparatus 136 is configured to remove and/or eliminate gasses from the fluid 308 to prevent formation of gas bubbles within the catheter system 100. More specifically, the fluid degassing apparatus 136 is configured to remove and/or eliminate gasses from the fluid 308 by restricting the flow of and expelling or exhausting gasses present in the fluid 308, and/or by pulling gasses dissolved in the fluid 308 out of solution and expelling or exhausting the gasses out of the catheter system 100. Accordingly, fluid that passes through the fluid degassing apparatus 136 and directed to the catheter 104 is free of or substantially free of gasses.

FIG. 3 illustrates three examples of fluid degassing apparatus 136 suitable for use in the catheter system 100, including a multi-chamber system 310, a gas filter 312, and a centrifugal separator 314. It should be understood that the fluid degassing apparatus shown and described with reference to FIG. 3 are non-exhaustive, and that other types of fluid degassing apparatus may be used with the catheter system 100. Moreover, it should be understood that the multi-chamber system 310, the gas filter 312, and the centrifugal separator 314 may be used separately in the catheter system 100, or in any combination (e.g., connected in series or parallel with one another) in the catheter system 100 to remove and/or eliminate gasses from the fluid 308.

Figure 4:
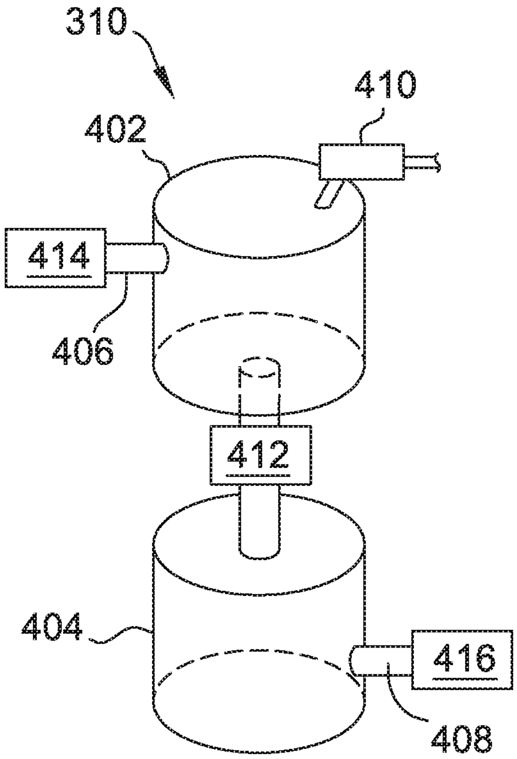
FIG. 4 is an enlarged schematic view of one exemplary embodiment of a fluid degassing apparatus in the form of a multi-chamber system suitable for use in the irrigated catheter system of FIG. 1.

FIG. 4 is an enlarged schematic view of the multi-chamber system 310 shown in FIG. 3. The multi-chamber system 310 includes a vacuum chamber 402 and a fluid reservoir 404 fluidly coupled downstream of the vacuum chamber 402. The vacuum chamber 402 includes a fluid inlet 406 (e.g., fluid inlet 302) for receiving the fluid 308 from the fluid source 132, and the fluid reservoir 404 includes a fluid outlet 408 (e.g., fluid outlet 304) for supplying the fluid 308 to the catheter 104. Although the multi-chamber system 310 is illustrated with a single vacuum chamber 402 and a single fluid reservoir 404, it should be understood that the multi-chamber system 310 may include more than a single vacuum chamber 402 and more than a single fluid reservoir 404 in other embodiments. Additionally, the multi-chamber system 310 may include chambers other than the vacuum chamber 402 and the fluid reservoir 404.

The multi-chamber system 310 is configured to remove gas from the fluid 308 by subjecting the fluid 308 to a vacuum or negative pressure within the vacuum chamber 402 for a certain dwell time. By subjecting the fluid 308 to a vacuum or negative pressure, gasses present in the fluid are removed and gasses dissolved in the fluid can be pulled out of solution. Once the fluid 308 is held under vacuum for the dwell time, the degassed fluid is allowed to pass into the fluid reservoir 404, wherein the degassed fluid is held until it is needed for irrigation of the catheter 104.

A suitable vacuum source 410 is coupled to the vacuum chamber 402 and is selectively operable to generate negative pressure within the vacuum chamber 402. The vacuum source 410 may include any suitable device for generating vacuum within the vacuum chamber 402, including, for example and without limitation, a vacuum pump and an evacuated container. In some embodiments, the vacuum source 410 can be communicatively coupled to the control system 154 for controlling the vacuum source 410 and selectively applying vacuum to the vacuum chamber 402.

The multi-chamber system 310 also includes a control valve 412 configured to control fluid flow between the vacuum chamber 402 and the fluid reservoir 404. The control valve 412 is selectively positionable between an open position, in which fluid is permitted to flow from the vacuum chamber 402 to the fluid reservoir 404, and a closed position, in which the control valve 412 inhibits fluid flow from the vacuum chamber 402 to the fluid reservoir 404. The control valve 412 is fluidly coupled between the vacuum chamber 402 and the fluid reservoir 404. That is, the control valve 412 is coupled between a fluid outlet of the vacuum chamber 402 and a fluid inlet of the fluid reservoir 404. The control valve 412 can include any suitable valve that enables the multi-chamber system 310 to function as described herein, including electrically-actuated valves, such as solenoid valves, and manually-actuated valves. In some embodiments, the control valve 412 is communicatively coupled to the control system 154 for controlling the position of the valve 412. In such embodiments, the control system 154 can be configured to actuate the control valve 412 to the closed position such that fluid is held within the vacuum chamber 402 under vacuum for the dwell time to remove gas from the fluid and, after the dwell time has elapsed, actuate the control valve 412 to the open position to allow degassed fluid to flow from the vacuum chamber 402 into the fluid reservoir 404. Additionally, in some embodiments, after the dwell time has elapsed, the pressure within the vacuum chamber 402 may be allowed to reach atmospheric pressure or near atmospheric pressure (e.g., by disconnecting or shutting off the vacuum source 410) to facilitate fluid flow from the vacuum chamber 402 to the fluid reservoir 404. The multi-chamber system 310 may include other suitable valves and flow control devices including, for example and without limitation, an inlet valve 414 to control the supply of fluid into the vacuum chamber 402, and an outlet valve 416 to control the supply of fluid out of the fluid reservoir 404.

After degassed fluid is supplied to the fluid reservoir 404, the degassed fluid can be supplied to the catheter 104 for use as irrigation fluid, for example, by pumping the fluid from the fluid reservoir 404 to the fluid delivery tube 130 using the pump 134. Additionally, in some embodiments, additional fluid can be supplied to the vacuum chamber 402 for degassing while fluid is simultaneously drawn from the fluid reservoir 404. After the fluid in the vacuum chamber 402 has been degassed (e.g., held in the vacuum chamber 402 under suitable vacuum for the dwell time), the control valve 412 is opened and the degassed fluid is supplied to the fluid reservoir 404. In this way, the multi-chamber system 310 can provide a "batch" process of suppling irrigation fluid to the catheter system 100, where batches of degassed fluid are periodically or intermittently supplied to the fluid reservoir 404 during a medical procedure.

Figure 5:
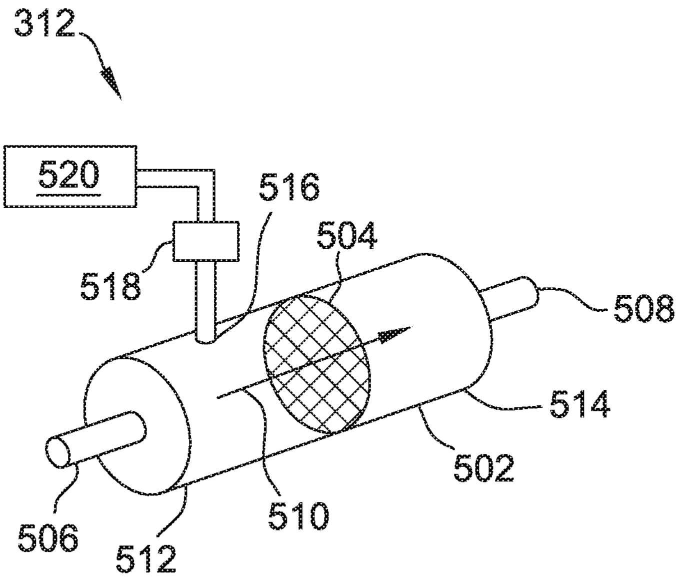
FIG. 5 is an enlarged schematic view of another exemplary embodiment of a fluid degassing apparatus in the form of a gas filter suitable for use in the irrigated catheter system of FIG. 1.

FIG. 5 is an enlarged schematic view of the gas filter 312 shown in FIG. 3. As shown in FIG. 5, the gas filter 312 includes a fluid-tight housing 502 and a liquid permeable membrane 504 disposed within the housing 502. The housing 502 includes a fluid inlet 506 (e.g., fluid inlet 302) and a fluid outlet 508 (e.g., fluid outlet 304), and defines a fluid flow path, indicated by arrow 510, extending from the fluid inlet 506 to the fluid outlet 508. The fluid-tight construction of housing 502 prevents fluids from entering or leaving the housing 502 except through intended openings, such as the inlet 506, the outlet 508, and vent openings, as described further herein. The permeable membrane 504 is disposed within the fluid flow path 510 such that all fluid flowing from the inlet 506 to the outlet 508 flows through the permeable membrane 504.

The permeable membrane 504 separates or divides the housing 502 into an upstream side 512 and a downstream side 514. In the illustrated embodiment, the permeable membrane 504 is configured to restrict or inhibit passage of gas therethrough such that gas collects or accumulates on the upstream side 512 of the membrane 504. Additionally or alternatively, the permeable membrane 504 can be configured to pull dissolved gas out of solution such that gas is generated as the fluid 308 flows through membrane 504 and collects or accumulates on the downstream side 514 of the membrane 504. In some embodiments, the permeable membrane 504 and/or the housing 502 may be replaceable, for example, after use during a procedure. That is, the permeable membrane 504 and/or the housing 502 may be configured for a single use, and be disposed of after a single use. In such embodiments, the remaining components of the gas filter 312 may be configured to receive a replacement permeable membrane 504 and/or a replacement housing 502.

The housing 502 is suitably sized and shaped to permit accumulation of gas within the upstream side 512 and/or the downstream side 514 of housing. Additionally, in some embodiments, such as the embodiment illustrated in FIG. 5, the gas filter 312 can include one or more vent openings 516 configured to expel accumulated gas from within the housing 502. The vent openings 516 can be located on the upstream side 512 of the housing 502 and/or on the downstream side 514 of the housing 502. Additionally, in such embodiments, the gas filter 312 can include a check valve 518 coupled to the vent opening 516 to control the flow of gas through the vent opening 516. In particular, the check valve 518 can be configured as a one-way check valve to inhibit fluid flow into the housing 502, and permit only gas flow out of the housing 502. Further, in some embodiments, a vacuum source 520 (e.g., vacuum source 410) can be coupled to the vent opening 516 to apply a negative pressure thereto to facilitate removing gas from the fluid 308 and/or from within the housing 502. In some embodiments, for example, the vacuum source 520 can be configured to selectively apply a vacuum to the vent opening 516 to remove accumulated gas from within the housing 502. The vacuum source 520 can be communicatively coupled to the control system 154 for controlling the application of vacuum to the vent opening 516.

Although the gas filter 312 is illustrated in a horizontal orientation (i.e., the elongate axis of the housing 502 is oriented horizontally and the membrane 504 is oriented vertically) in FIG. 5, the gas filter 312 may be positioned in any suitable orientation that enables the gas filter 312 to function as described herein. In some embodiments, for example, the gas filter 312 may be oriented vertically (i.e., with the elongate axis of housing 502 oriented vertically and/or with the permeable membrane 504 oriented horizontally) so that gas filtered out and/or generated by fluid passing through the membrane 504 collects at one end of the housing 502. In one specific implementation, the gas filter 312 is oriented vertically with the inlet or upstream side of the housing 502 positioned vertically above the outlet or downstream side of the housing 502 such that fluid flowing through the gas filter 312 flows generally downward from the inlet 506 to the outlet 508. In such embodiments, gas collected and/or generated within the housing 502 can have a natural tendency to float upwards, towards the inlet 506, and collect or accumulate near the top of the housing 502. The gas can then be expelled or exhausted with a suitable vent opening (e.g., vent opening 516). Such an orientation of the gas filter 312 may facilitate removing gas from the fluid 308 before the fluid 308 is delivered to the catheter 104.

Referring again to FIG. 3, the centrifugal separator 314 is configured to separate gas from the fluid supplied by the fluid source 132 by subjecting the fluid 308 to centrifugal forces. The centrifugal separator 314 may include any suitable centrifugal separators known in the art that enables the fluid degassing apparatus 136 to function as described herein.

Figure 6:
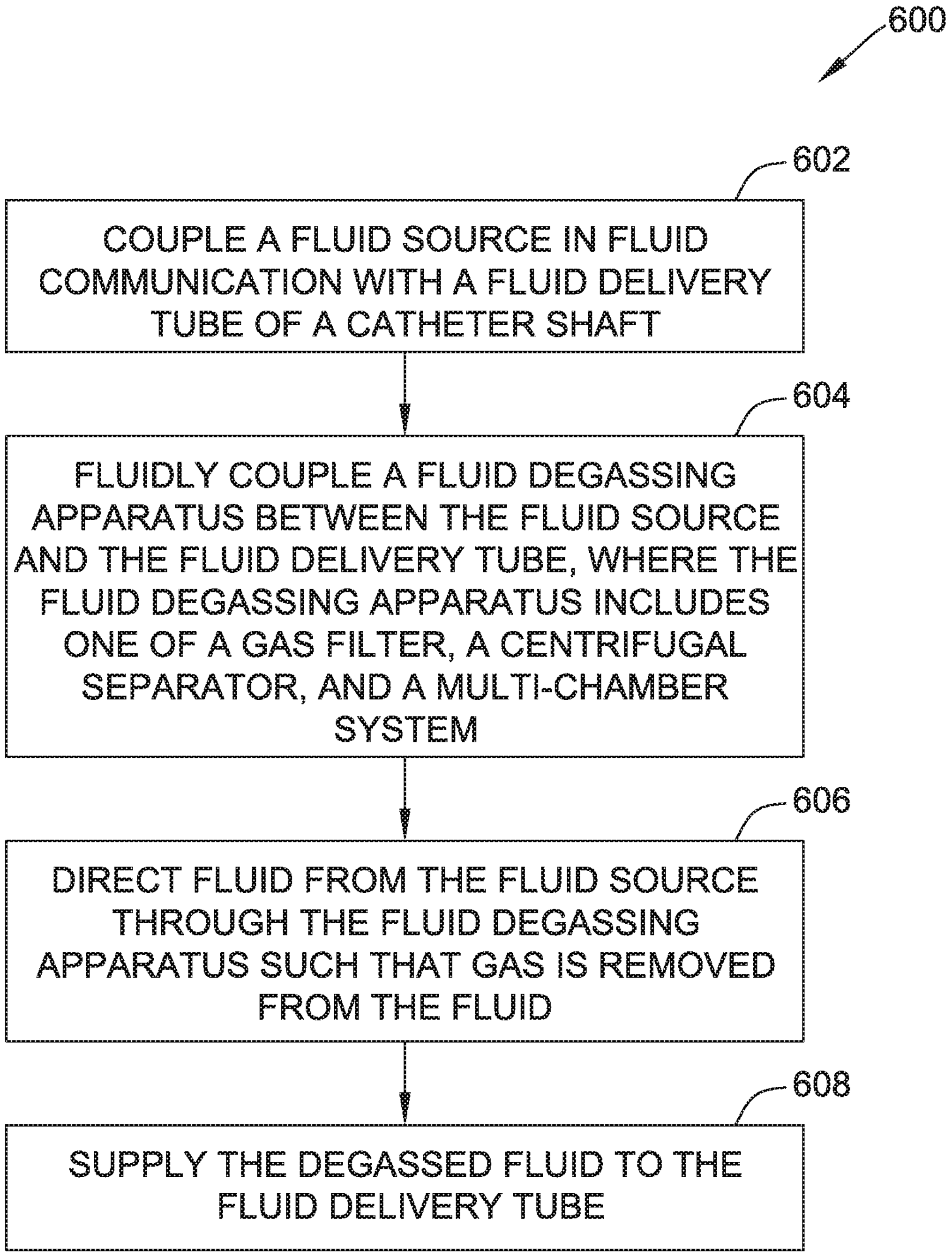
FIG. 6 is a flow diagram illustrating one embodiment of a method of supplying fluid to an irrigated catheter system.

FIG. 6 is a flow diagram illustrating one embodiment of a method 600 of supplying fluid to an irrigated catheter system, such as the irrigated catheter system 100 shown in FIG. 1. In the illustrated embodiment, the method 600 includes coupling 602 a fluid source (e.g., fluid source 132) in fluid communication with a fluid delivery tube (e.g., fluid delivery tube 130) of a catheter shaft (e.g., catheter shaft 112). The catheter shaft includes an electrode (e.g., electrode 118) coupled to a distal end thereof and in fluid communication with the fluid delivery tube.

The method 600 further includes fluidly coupling 604 a fluid degassing apparatus (e.g., fluid degassing apparatus 136) between the fluid source and the fluid delivery tube, where the fluid degassing apparatus includes one of a gas filter (e.g., gas filter 312), a centrifugal separator (e.g., centrifugal separator 314), and a multi-chamber system (e.g., multi-chamber system 310). The gas filter includes a permeable membrane disposed in a fluid-tight housing. The multi-chamber system includes a vacuum chamber and a fluid reservoir fluidly coupled downstream of the vacuum chamber. The method 600 further includes directing 606 fluid from the fluid source through the fluid degassing apparatus such that gas is removed from the fluid, and supplying 608 the degassed fluid to the fluid delivery tube. In embodiments where the fluid degassing apparatus includes the multi-chamber system, directing 606 fluid from the fluid source through the fluid degassing apparatus may include directing the fluid into the vacuum chamber, subjecting the fluid to vacuum for a dwell time within the vacuum chamber to remove gas from the fluid, and directing the degassed fluid to the fluid reservoir after the dwell time has elapsed. In embodiments where the fluid degassing apparatus includes the gas filter, the method 600 may further include expelling accumulated gas from within the fluid-tight housing through a vent opening.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Systems and methods of the present disclosure facilitate improving catheter procedures, for example, by improving the accuracy of catheter sensor data and reducing the likelihood of air-embolism formation. In particular, the catheter systems and methods disclosed herein utilize in-line fluid degassing apparatus to remove, reduce, and/or eliminate gas from fluid supplied to the catheter during medical procedures, such as irrigant fluid. By removing or reducing gas from the fluid, the systems and methods herein reduce the likelihood of gas bubbles accumulating within the catheter system, which could otherwise cause inaccurate temperature sensor readouts and/or formation of gas bubbles that can lead to air embolisms. Accordingly, the systems and methods of the present disclosure facilitate improving catheter procedures.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An irrigated catheter system comprising:

a catheter shaft comprising a fluid delivery tube;

an electrode coupled to the catheter shaft at a distal end thereof and coupled in fluid communication with the fluid delivery tube;

a fluid source coupled in fluid communication with the fluid delivery tube for supplying fluid thereto; and a fluid degassing apparatus fluidly coupled between the fluid source and the fluid delivery tube such that the fluid flows through the fluid degassing apparatus, wherein the fluid degassing apparatus comprises:

a multi-chamber system comprising a vacuum chamber and a fluid reservoir fluidly coupled downstream of the vacuum chamber.

2. The irrigated catheter system of claim 1, wherein the multi-chamber system comprises a control valve configured to control fluid flow between the vacuum chamber and the fluid reservoir, wherein the control valve is selectively positionable between an open position, in which fluid is permitted to flow from the vacuum chamber to the fluid reservoir, and a closed position, in which the control valve inhibits fluid flow from the vacuum chamber to the fluid reservoir.

3. The irrigated catheter system of claim 2, wherein the control valve is communicatively coupled to a control system of the catheter system, wherein the control system is configured to:

actuate the control valve to the closed position such that fluid is held within the vacuum chamber under vacuum for a dwell time to remove gas from the fluid;

and actuate the control valve to the open position to allow degassed fluid to flow from the vacuum chamber into the fluid reservoir.

4. The irrigated catheter system of claim 1 further comprising a vacuum source coupled to the vacuum chamber and selectively operable to generate negative pressure within the vacuum chamber.

5. The irrigated catheter system of claim 1, wherein the vacuum chamber includes a fluid inlet for receiving fluid from the fluid source, and wherein the fluid reservoir includes a fluid outlet for supplying degassed fluid to the fluid delivery tube.

6. The irrigated catheter system of claim 1, wherein the fluid degassing apparatus comprises a fluid inlet and a fluid outlet, wherein at least one of the fluid inlet and the fluid outlet comprises a leak-free fluid fitting.

7. The irrigated catheter system of claim 6, wherein the leak-free fluid fitting comprises a Luer adapter.

8. The irrigated catheter system of claim 1, further comprising a pump fluidly coupled to the fluid source and configured to pump fluid from the fluid source, through the fluid degassing apparatus, to the fluid delivery tube.

9. The irrigated catheter system of claim 1, wherein the electrode comprises an ablation electrode.

10. The irrigated catheter system of claim 1, wherein the electrode comprises a positioning electrode.

11. A method of supplying fluid to an irrigated catheter system, said method comprising:

coupling a fluid source in fluid communication with a fluid delivery tube of a catheter shaft, the catheter shaft including an electrode coupled to a distal end thereof and in fluid communication with the fluid delivery tube;

fluidly coupling a fluid degassing apparatus between the fluid source and the fluid delivery tube, wherein the fluid degassing apparatus comprises:

a multi-chamber system comprising a vacuum chamber and a fluid reservoir fluidly coupled downstream of the vacuum chamber;

directing fluid from the fluid source through the fluid degassing apparatus such that gas is removed from the fluid; and supplying the degassed fluid to the fluid delivery tube.

12. The method of claim 11, wherein directing fluid from the fluid source through the fluid degassing apparatus further comprises:

directing the fluid into the vacuum chamber;

subjecting the fluid to vacuum for a dwell time within the vacuum chamber to remove gas from the fluid; and directing the degassed fluid to the fluid reservoir after the dwell time has elapsed.

13. An irrigated ablation catheter system comprising:

a catheter shaft comprising a fluid delivery tube;

an ablation electrode coupled to the catheter shaft at a distal end thereof and in fluid communication with the fluid delivery tube;

an ablation generator electrically coupled to the electrode and configured to supply ablative energy thereto;

a fluid source coupled in fluid communication with the fluid delivery tube;

a pump coupled in fluid communication with the fluid source and configured to pump fluid from the fluid source to the fluid delivery tube; and a fluid degassing apparatus fluidly coupled between the fluid source and the fluid delivery tube such that the fluid flows through the fluid degassing apparatus, wherein the fluid degassing apparatus comprises:

a multi-chamber system comprising a vacuum chamber and a fluid reservoir fluidly coupled downstream of the vacuum chamber.

* * * * *